US00PP22494P3

(12) United States Plant Patent

Maillard et al.

(10) Patent No.: US PP22,494 P3

(45) Date of Patent: Feb. 14, 2012

(54) NECTARINE TREE NAMED 'NECTABANG'

(50) Latin Name: ***Prunus persica* var. *nucipersica***
Varietal Denomination: NECTABANG

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 12/662,964

(22) Filed: May 13, 2010

(65) Prior Publication Data

US 2010/0293680 P1 Nov. 18, 2010

(30) Foreign Application Priority Data

May 18, 2009 (QZ) ..... PBR 2009/0927

(51) Int. Cl.
*A01H 5/00* (2006.01)

(52) U.S. Cl. ..... Plt./190

(58) Field of Classification Search ..... Plt./190
See application file for complete search history.

*Primary Examiner* — June Hwu

(74) *Attorney, Agent, or Firm* — Westerman, Hattori, Daniels & Adrian, LLP

(57) ABSTRACT

A new and distinct variety of nectarine tree, denominated 'NECTABANG', has fruits of very long shelf life without alteration before and after harvesting, a semi-sweet yellow flesh of high-eating quality and an attractive red skin. Fruits can be consumed crunchy or melting.

4 Drawing Sheets

Botanical classification: *Prunus persica* var. *nucipersica*.
Variety denomination: 'NECTABANG'.

This application claims priority of Community plant variety right No. 2009/0927 filed on May 18, 2009, which is hereby incorporated by reference in its entirety.

BACKGROUND OF THE VARIETY

The present invention relates to a new and distinct variety of *Prunus persica* var. *nucipersica* yellow nectarine tree, which has been given the denomination 'NECTABANG'. This tree, named 'NECTABANG', produces clingstone fruits of good eating quality for fresh market in June in the 66—Pyrénées-Orientales departement—France. Contrast is made to 'Nectaprima' (U.S. Plant Pat. No. 17,583) and 'Nectapink' (U.S. Plant Pat. No. 17,584) yellow nectarine trees, standard varieties, for reliable description. 'NECTABANG' is a promising candidate for commercial success in that it has an evenness of maturity, and produces regular fruits in large quantity and with a high productivity. It was chosen because of its hardiness and fruit lifetime before and after harvest, and because of its aromatic semi sweet taste.

ORIGIN OF THE VARIETY

'NECTABANG' nectarine tree originated in a cultivated area of the south of France, in the 66—Pyrénées-Orientales departement—France where it was tested. This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontagne': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'NECTABANG' variety was selected from controlled crosses between the 'Nectaprima' (U.S. Plant Pat. No. 17,583) yellow nectarine tree (female parent) and the 'Nectapink' (U.S. Plant Pat. No. 17,584) yellow nectarine tree (male parent). 'NECTABANG' is a variety which has a number of flowers smaller than the number of flowers on 'Nectaprima' (U.S. Plant Pat. No. 17,583) trees. Moreover, 'NECTABANG' fruits are bigger, have a more intense skin colour and a sweeter taste than 'Nectaprima' (U.S. Plant Pat. No. 17,583) fruits. Compared to the male parent 'Nectapink', (U.S. Plant Pat. No. 17,584) 'NECTABANG' variety ripens 45 days earlier and 'NECTABANG' fruits are more appealing. 'NECTABANG' was provisionally designated, tested and genetically identified by a genetic profile, as 4N.05.141 NJASF 0503 and was registered at the Official Catalogue of the Agriculture Ministry of the French Republic on Dec. 1, 2008 under number 1028953. It was obtained by hybridizing and propagated by grafting on a 'Franc Inra Montclar' (non-patented) or 'Cadaman' (non-patented) or 'INRA GF 677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of nectarine tree blooms in March at Perpignan in the Pyrénées-Orientales departement, France. More particularly, it generally blooms between March 1st and March 10th, approximately at the same time than the 'Nectaprima' (U.S. Plant Pat. No. 17,583) variety.

The first fruit of 'NECTABANG' ripens in middle June, generally about one week after the 'Nectaprima' (U.S. Plant Pat. No. 17,583) variety. More particularly, it approximately ripens between June 10th and June 25th under normal climatic conditions. The fruits of NECTABANG variety ripen about 8 weeks before NECTATOP (U.S. Plant Pat. No. 21,141) fruits and 10 weeks before NECTAPI (U.S. Plant Pat. No. 21,156) fruits. Indeed, NECTATOP and NECTAPI fruits ripen respectively in early August and in early September, whereas NECTABANG fruits ripen in early June.

DESCRIPTION OF THE DRAWINGS

In the accompanying drawing, which are as nearly true as it is reasonably possible to make in a color illustration of this type.

Figure 1:
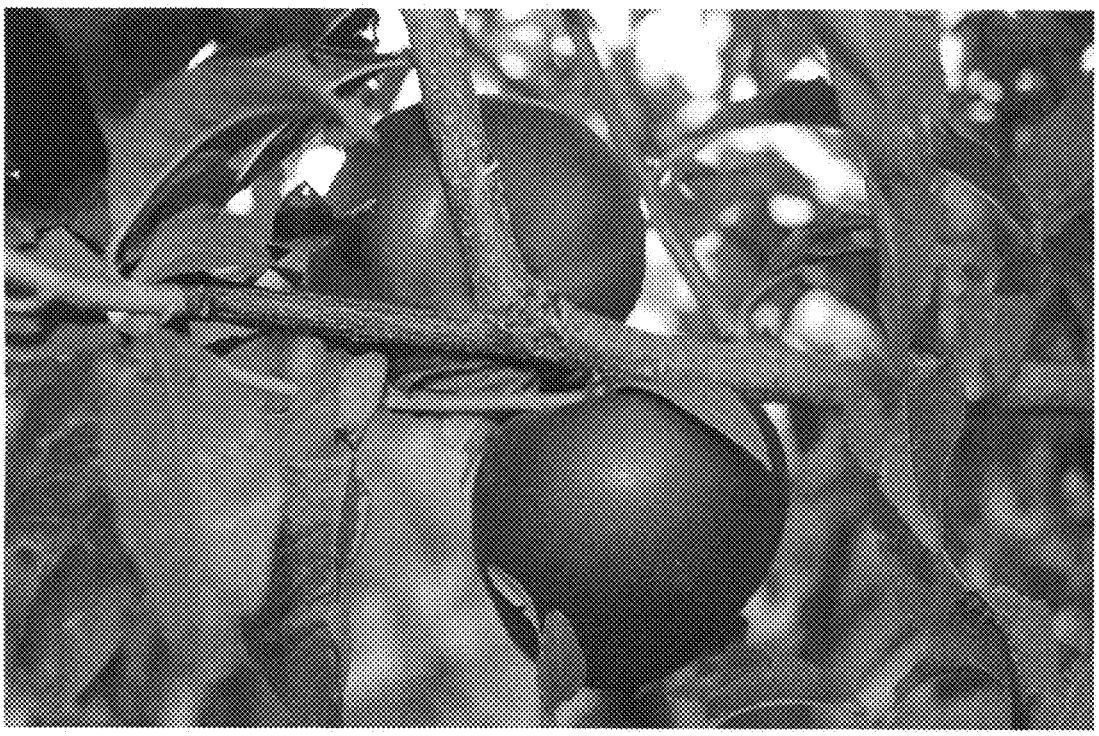
FIG. 1 is a color photograph, which shows typical fruit specimens on a tree of the new variety and leaves of the new variety in orchard.
Figure 2:
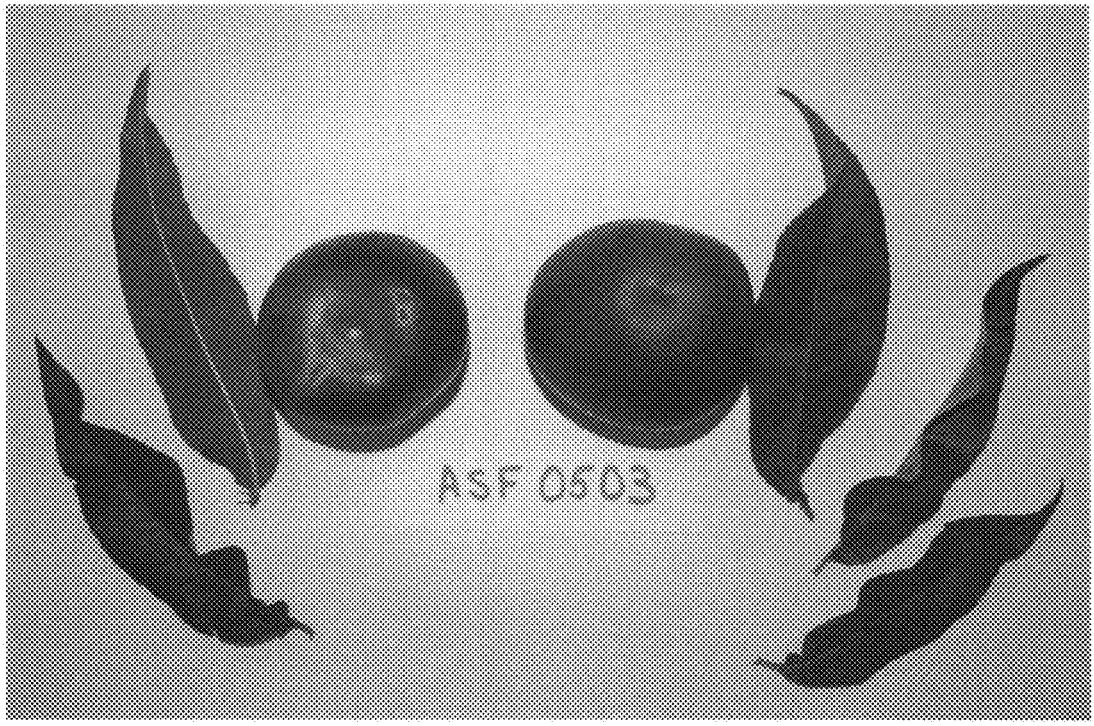
FIG. 2 is a color photograph, which shows two whole fruit sufficiently mature for harvesting and shipment and five leaves of the new variety.
Figure 3:
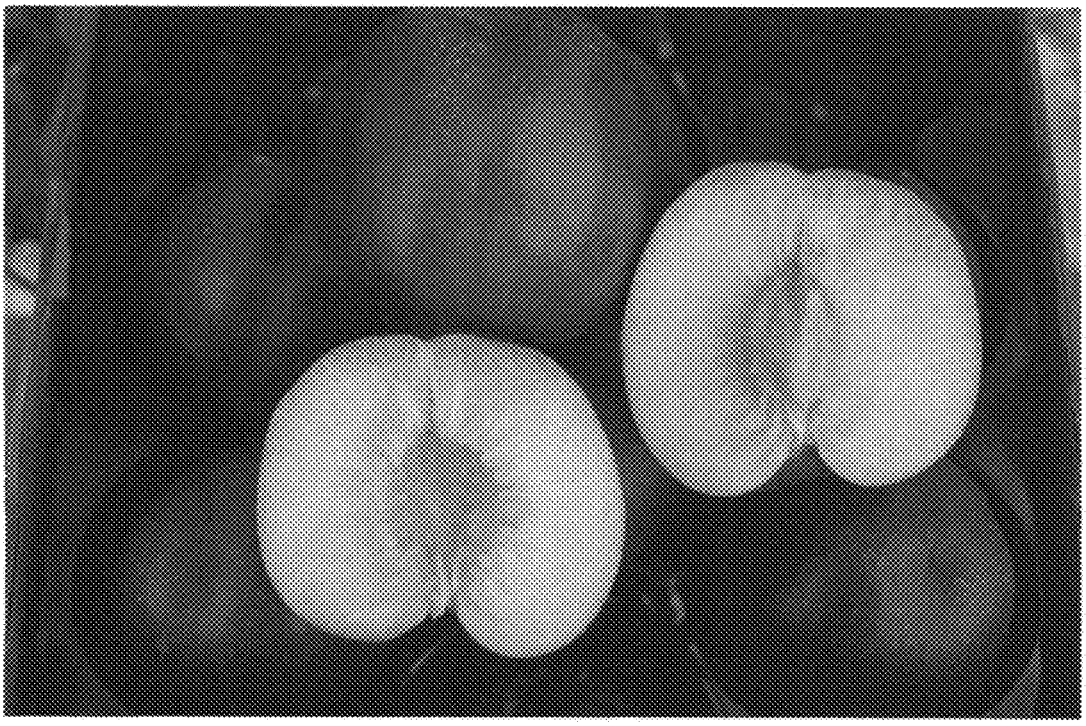
FIG. 3 is a color photograph, which shows a fruit cut in half for depicting the fruit flesh and the pit cavity of the new variety.
Figure 4:
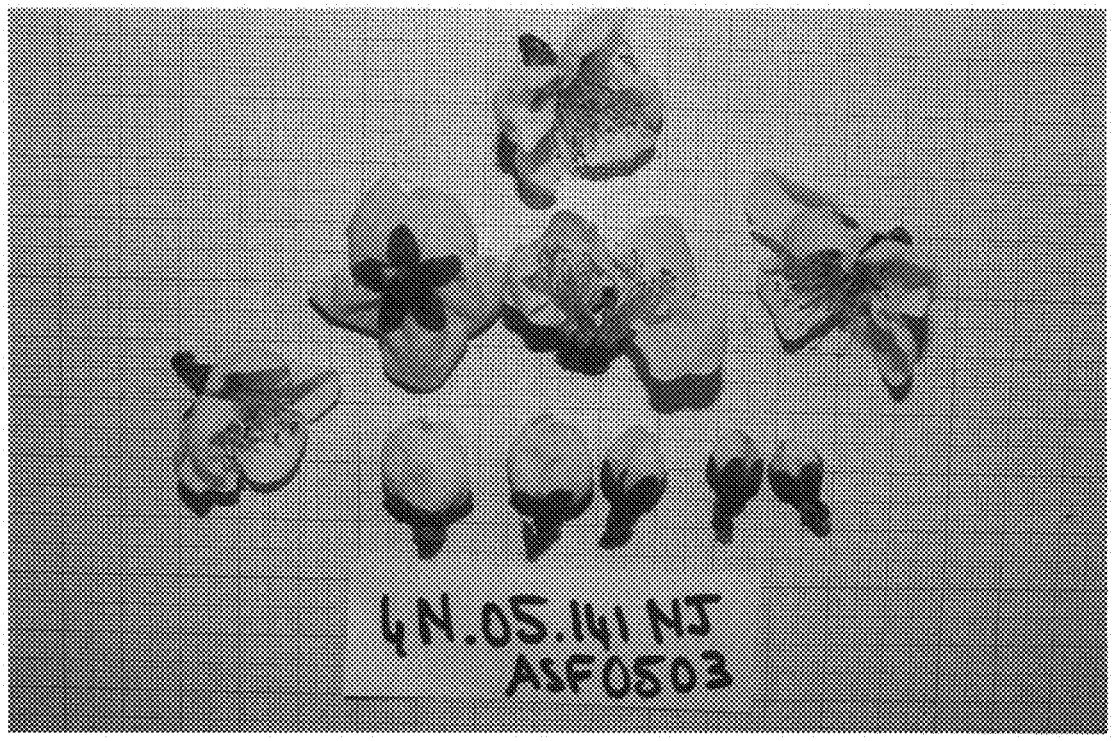
FIG. 4 is a color photograph with reverse and size views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition.

Trees are vigorous and of medium stature, half-standing in a semi-spread to semi-upright out aspect. The anthocyanic coloration of the flowering shoot is present excluding brushwood side away from sun. Flowering begins semi-early in springtime. The type of flower is showy with generally medium to large petals of medium pink color. Leaf glands are present and reniform. Time of maturity for consumption is early. The fruit flesh is yellow with only rare red pigmentation. Fruit skin color features an homogeneous dark red blush. Fruit taste is semi-sweet.

The 'NECTABANG' variety blooms almost at the same time and ripens approximately one week after the 'Nectaprima' variety (U.S. Plant Pat. No. 17,583). However, the number of flowers on 'NECTABANG' trees is smaller than the number of flowers on 'Nectaprima' trees (only 40 flowers per meter instead of 50-60 flowers per meter). Compared to 'Nectaprima' fruits, 'NECTABANG' fruits are more appealing because their skin color is more intense and fruits are bigger and with a sweeter taste. They also have a longer shelf life.

The new variety male parent, which is 'Nectapink' (U.S. Plant Pat. No. 17,584), comparatively ripens approximately 45 days after the new variety. 'NECTABANG' fruits are more appealing with respect to their general shape and color.

DETAILED DESCRIPTION

Referring more specifically to the pomological details of this new and distinct variety of nectarine tree, the following was observed on trees in their third growing season under the ecological conditions prevailing at the orchards located near the town of Elne, Pyrénées-Orientales departement, France. All observations have been done on rootstock cultivars. Used rootstocks were 'Franc Inra Montclar' (non-patented) trees or 'Cadaman' (non-patented) trees or 'INRA GF 677' (non-patented) trees. All major color code designations are by reference to The R.H.S. Colour Chart (Fourth Edition) provided by The Royal Horticultural Society of Great Britain.

Tree:

*Size.*—Generally — Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm with current season shoots length comprised.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigour.*—Considered average.

*Productivity.*—Very productive. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

*Bearer.*—Very regular. Fruit set has been heavy during the years of observation and thinning of 1 fruit on 3 was necessary every year.

*Form.*—The 'NECTABANG' variety has naturally a semi-spread to semi-upright shape.

*Density.*—Considered dense.

*Hardiness.*—The present tree was grown and evaluated in France. The variety appeared to be hardy under typical central Pyrénées-Orientales departement climatic conditions. Experimentations on different sites with winter chilling requirement comprised between 350 and 1200 hours showed a good behavior of the tree in all cases. Ascertained temperatures as low as −12 degrees Celsius in winter caused no damages to the tree. The tree was also very resistant to frosty springtime weather.

Trunk:

*Diameter.*—Approximately between 6.0 and 7.0 cm in diameter when measured at a distance of approximately 30 cm above the soil level.

*Bark texture.*—Considered rough.

*Lenticels.*—Numerous lenticels are present. The lenticels range in size from approximately 0.4 to 0.5 cm in width, and from 0.15 to 0.2 cm in height.

*Lenticel color.*—The outside of lenticels has a silver-grey color (RHS Grey 201 C), whereas the inside is considered brown (RHS Greyed Orange 166 B).

*Bark coloration.*—The bark has a silver-grey color (RHS Grey 201 C to RHS Black 202 C).

Branches:

*Size.*—Mature branches as well as current season shoots are medium for the variety.

*Diameter.*—Average as compared to other nectarine varieties. The current season shoots have a diameter from 6.0 to 7.0 millimeters, and branches of trees have a diameter comprised between 15.0 and 23.0 millimeters.

*Surface texture.*—Average, several years old wood has no furrowed appearance.

*Crotch angles.*—Primary branches are considered variable, but the crotch angles are generally between 60 and 80 degrees from the horizontal axis. This particular characteristic is not considered distinctive of the variety, however.

*Current season shoots.*—Surface texture — Substantially glabrous.

*Internode length.*—Generally 26.0 to 36.0 millimeters.

*Color of mature branches.*—Medium brown (RHS Grey Brown 199 A to B).

*Current seasons shoots.*—Color — The color of new shoot tips is considered a light yellow green (varying from RHS Yellow Green 144 A to RHS Yellow Green 144 C) on lower part of new shoot tips, whereas the upper part is colored in purple brown to red brown (RHS Greyed Purple Group 187 A to B to RHS Greyed Red 182 A).

Leaves:

*Size.*—Considered medium to large for the species. The ratio leaf length/leaf width is below 3,4.

*Leaf length.*—Approximately 140 to 166 millimeters with petiole.

*Leaf width.*—Approximately 45 to 63 millimeters.

*Leaf base shape.*—Concave.

*Leaf form.*—Lanceolate.

*Leaf tip form.*—Small and acuminate.

*Leaf color.*—Upper leaf surface — Dark Green (RHS Green 137 A). Lower surface — Medium Green (RHS Green 137 B to 137 C).

*Leaf texture.*—Smooth and glabrous.

*Leaf venation.*—Pinnately veined.

*Mid-vein.*—Color — Generally a Light yellow green (RHS Yellow Green 145 D to 145 C).

*Leaf margins.*—Slightly undulating.

*Form.*—Considered slightly dentate.

*Uniformity.*—Leaves are isolated or grouped by 2 or 3. In this last case, one leaf of normal size is found with one or two smaller leaves (50% smaller at least).

*Leaf petioles.*—Size — Considered medium. Length — About 8.0 to 12.0 mm. Diameter — About 2.0 mm. Color — Light yellow green (RHS Yellow Green 144 D to 144 C).

*Leaf glands.*—Size — Considered medium, about 1.5 mm. Number — 2 to 4 glands. Type — Reniform. Color — On young leaves, leaf glands color is considered a pale green (RHS Green 144 B to A). On older leaves, leaf glands color turn to a dark brown (RHS Grey Brown 199 A to 199 B).

*Leaf stipules.*—Generally — No leaf stipules were observed. But as seen in the characteristic relative to the leaves uniformity, it is possible to find leaves by groups of 2 or 3, with a normal-size leaf and smaller ones.

Flowers:

*Flower buds.*—Generally — At pre-floral stage of development, the floral buds are conic in form with a round tip. Their form is evolving until blooming, with variables dimensions. Just before blooming, floral buds are approximately 12.0 millimeters wide and approximately 18.0 millimeters long.

*Flower buds.*—Color — This characteristic is dependent upon the proximity to bloom. At pre-floral stage of development, the bottom of the flowers buds, formed by sepals, is of purple-brown color (Generally RHS Greyed Purple 183 A); the corolla, formed by petals, is generally of medium pink color (varying from RHS Red Purple 65 B to C). Petals color shows an evolution until the end of flowering. The buds are considered hardy under typical central Pyrénées-Orientales departement climatic conditions.

*Hardiness.*—No winter injury was noted during the last several years of evaluation in the central Pyrénées Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—Generally early March. The first bloom was observed on Feb. 28, 2002.

*Blooming time.*—Considered semi-early in relative comparison to other commercial nectarine cultivars grown in the Pyrénées-Orientales departement, France. The date of full bloom is observed in March, more particularly between March 1$^{st}$ and March 10$^{th}$. The date of bloom varies slightly with climatic conditions and cultural practices. Last observed blooming times were from Mar. 9, 2006 to Mar. 13, 2006, then from Mar. 5, 2007 to Mar. 15, 2007, then from Feb. 19, 2008 to Mar. 1$^{st}$, 2008 (approximately 10 days sooner than during a normal year), then from Feb. 26, 2009 to Mar. 11, 2009.

*Duration of bloom.*—Approximately 12 days. This characteristic varies slightly with the prevailing climatic conditions.

*Flower type.*—The variety is considered to have showy type flowers.

*Flower size.*—Considered medium to large. Flower diameter at full bloom is approximately between 30.0 to 40.0 millimeters.

*Bloom quantity.*—Considered average, approximately between 35 and 40 flowers per meter.

*Flower bud frequency.*—Generally 2 flower buds appear per node, occasionally 1.

*Petal size.*—Generally — Considered medium to large for the species.

*Length.*—Generally between 20.0 millimeters.

*Width.*—Generally between 21.0 millimeters.

*Petal form.*—Rounded.

*Petal count.*—Generally 5.

*Petal texture.*—Smooth and glabrous.

*Petal color.*—Medium Pink (RHS Red Purple 65 B to C) slightly darkening over time.

*Fragrance.*—Slight.

*Petal claw.*—Form — The claw is considered to have a conic form with a slighty rounded extremity.

Length — Approximately between 5.0 and 6.0 millimeters. Width — Approximately 4.0 millimeters.

*Petal margins.*—Generally slightly undulated.

*Petal apex.*—Generally — The petal apices have a large dome-shaped form.

*Flower pedicel.*—Length — Considered medium to long and having an average length of approximately 3.0 to 5.0 millimeters. Diameter — Approximately 2.0 millimeters. Color — A medium brown (RHS Grey Brown N199 B to 199 C).

*Floral nectaries.*—Color — A flat golden orange (approximately RHS Greyed Red 178 C to B).

*Calyx.*—Internal surface texture — Smooth and glabrous. Color — The outer surface of the calyx is considered of Purple-brown (RHS Greyed Purple 183 A) color.

*Sepals.*—Surface texture — The outer surface has a fine pubescent texture. Size — Generally medium. Color — Red (Approximately RHS Greyed Red 178 A).

*Average number of stamens per flower.*—About 40 stamens per flower.

*Anthers.*—Generally — Medium in length. Color — Red to orange-red color (approximately RHS Greyed Purple Group 178 A). Anthers are becoming yellow at maturity.

*Pollen production.*—Pollen is abundant, and has a yellow color (Approximately RHS Yellow Orange 17 B to C). The present variety is considered self fruitful (self-pollinating).

*Filaments.*—Size — Variable in length, approximately 8.0 to 13.0 millimeters in length. Filaments length is generally approximately equal to pistil's length.

*Color.*—Considered light pink (varying from RHS Red Purple 62 C to D) darkening over time.

*Pistil.*—Number — Usually 1. Generally — Medium in size. Length — Approximately 16.0 to 18.0 millimeters including the ovary; Generally approximately equal to filament's length. Color — Considered a very pale green (varying from RHS Yellow Green 150 D Group to RHS Yellow Green 151 D Group). Surface texture — The variety has a glabrous pistil.

Fruit:

*Maturity when described.*—Very firm ripe condition (shipping ripe).

*Date of first picking.*—Jun. 17, 2002. The picking generally occurs between June $10^{th}$ and June $25^{th}$ under normal climatic conditions. The date of harvest varies slightly with the prevailing climatic conditions.

*Date of last picking.*—Jun. 25, 2002. Picking can generally be achieved with only 2 harvests within approximately 8 days. Last known picking times were from Jun. 20, 2006 to Jun. 26, 2006, then from June 17 to Jun. 25, 2007, then from June 7 to Jun. 12, 2008, then from June 15 to Jun. 22, 2009.

*Size.*—Generally — Considered medium to large, and homogenous between fruits.

*Average cheek diameter.*—Approximately 65.0 to 73.0 millimeters.

*Average axial diameter.*—Approximately 68.0 to 75.0 millimeters.

*Typical weight.*—Approximately between 150.0 and 200.0 grams. This characteristic is high dependent upon the prevailing cultural practices, and therefore is not particularly distinctive of the variety.

*Fruit form.*—Generally — Round to slightly oblate. The fruit is generally uniform in symmetry viewed from the suture's plane.

*Fruit suture.*—Very shallow and smooth, extending from the base to the apex. No apparent callousing or stitching exists along the suture line.

*Suture.*—Color — This has generally a color similar to the whole fruit color, a dark red blush (RHS Greyed Purple 185 A) over a orange-red ground (Varying from RHS Orange Red N 34 A to RHS Orange Red 34 B).

*Ventral surface.*—Form — Smooth.

*Apex.*—Non-prominent, small.

*Base.*—Wide-mouthed, shallow.

*Stem cavity.*—Average depth of the stem cavity is about 0.7 cm. Average width is about 1.5 cm.

*Fruit skin.*—Thickness — Considered very thick and strong, and very tenacious to the flesh to tenacious to the flesh depending on stage of maturity. Texture — Glabrous. Taste — Semi-sweet with a high level of sugar, aromatic. Tendency to crack — None observed.

*Color.*—Blush color — This blush color is generally a dark red blush (RHS Greyed Purple 185 A). The red blush covers between 80% and 90% of the fruit skin surface. Ground color — An orange-red (RHS Orange Red N 34 A to RHS Orange Red 34 B).

*Fruit stem.*—Medium in length, approximately 6.0 millimeters.

*Diameter.*—Approximately 4.0 millimeters.

*Color.*—Pale green (RHS Yellow Green 145A to 145 B).

*Flesh.*—Ripens — Very evenly, homogenous, long shelf-life of the fruit. Texture — Very firm, very dense, juicy at harvest maturity stage. Fibers — No fibers. Aroma — Pronounced. Eating quality — Considered very good and aromatic. Flavor — Considered semi-sweet. The Brix is generally superior to 12.0 degrees. Acidity is comprised between 6 and 9 meq/100 ml. The flavor is considered aromatic. The flesh is juicy. Juice — Very juicy at complete maturity. Brix — Generally superior to 12.0 degrees. This characteristic varies slightly with the number of fruit per tree, the prevailing cultural practices and the surrounding climatic conditions. Flesh color — Generally Yellow Orange (RHS Yellow Orange 16 B to C) and generally without red pigmentation inside the stone cavity. However, very occasionally, and depending of fruits and their stage of maturity, a very slight red pigmentation can appear inside the flesh and inside the stone cavity. Compared to other nectarine cultivars, this appearance of pigmentation is considered rare and, when found, is considered very slight.

Stone:

*Type.*—Clingstone.

*Size.*—Considered medium to large for the variety. The stone size varies significantly depending upon the tree vigor, load and prevailing growing conditions.

*Length.*—Approximately 26 to 31.0 millimeters.

*Width.*—Approximately 18 to 21.0 millimeters.

*Diameter.*—Approximately 16 to 18.0 millimeters.

*Form.*—Elliptic.

*Base.*—Straight.

*Apex.*—Shape — The stone apex has a small sharp tip.

*Stone cavity.*—Considered medium to large-sized, with an elliptic-form. Stone cavity's dimensions correspond to the stone's dimensions.

*Stone surface.*—Surface texture — The pit is transversely furrowed on its entire surface. Furrows are more pronounced toward the apex. The stone is pitted toward the base. Relief is generally prominent and present basally. Ridges — The surface texture is generally characterized by more prominent ridges along the ventral edges and is more prominent at the apical tip.

*Ventral edge.*—Width — Considered small to medium, and having a dimension of approximately 2.0 millimeters at mid-suture.

*Dorsal edge.*—Shape — Grooved.

*Stone color.*—The color of the dry stone is generally a light orange-brown (RHS Greyed Orange 173 C to D).

*Tendency to split.*—Splitting is absent or very low, depending on climatic conditions between the blooming period and the hardening of the stone.

*Kernel.*—Size — The kernel is considered medium. Length — About 20.0 millimeters. Width — About 12.0 millimeters. Thickness — About 3.0 to 4.0 millimeters. Form — Considered flattened and elliptic. Pellicle — Pubescent. Color — The kernel skin is brown-orange (RHS Greyed Orange 167 C) with darker brown-orange streaks (RHS Greyed Orange 166 C). The almond, which is the seed of the kernel, is cream-white (RHS Orange White 159 D). The kernel and its embryo are mature at the time of fruit maturity.

Use: The subject variety 'NECTABANG' is considered to be a nectarine tree of the early season of maturity, and which produces aromatic semi-sweet fruit with a high level of sugars and a brix higher than 12 degrees. Fruits are excellent for uncooked consumption, crunchy or at full maturity. Due to their flesh quality, firmness and density, they can also be commercialized as $4^{th}$ range product (packed fruit or fruit in bags for example). And they are also useful for both local and very long distance shipping because they have a long shelf life after harvesting, up to 1 month.

Keeping quality: Remarkable. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

Shipping quality: Considered very good. Fruits of the new nectarine variety showed minimal bruising of the flesh or skin damage after being subjected to normal harvesting and packing procedures. Its resistance to handling during harvest and packing and its long shelf life without alteration after harvest easily permit 3 to 4 weeks shipping at 2 degrees Celsius.

Resistance to insects and disease: No particular susceptibilities were noted. Under our climatic conditions, favourable to powdery mildew, and with few treatments, the present variety has not been shown to be very sensitive to powdery mildew, or conservation diseases and decay due to its thick and strong skin. No bacteriostatic substances were applied, and no symptom was observed.

Although the new variety of nectarine tree possesses the described characteristics when grown under the ecological conditions prevailing near the town of Elne, France, it should be understood that variations of the usual magnitude and characteristics incident to changes in growing conditions, fertilization, pruning, pest control and horticultural management are to be expected.

We claim:

1. A new and distinct variety of nectarine tree as illustrated and described, characterized by fruits of very long shelf life without alteration before and after harvesting, with a semi-sweet yellow flesh of high eating quality and an attractive skin, with a very high percentage of red blush.

* * * * *